(12) United States Patent
Horiuchi (10) Patent No.: US 6,754,301 B2
(45) Date of Patent: Jun. 22, 2004

(54) X-RAY CT SYSTEM, GANTRY APPARATUS AND OPERATION CONSOLE

(75) Inventor: Tetsuya Horiuchi, Tokyo (JP)

(73) Assignee: GE Medical systems Global Technology Company, LLC, Waukesha, WI (US)

(*) Notice: Subject to any disclaimer, the term of this patent is extended or adjusted under 35 U.S.C. 154(b) by 0 days.

(21) Appl. No.: 10/228,514

(22) Filed: Aug. 27, 2002

(65) Prior Publication Data

US 2003/0043961 A1 Mar. 6, 2003

(51) Int. Cl.⁷ .................................................. G01N 23/00
(52) U.S. Cl. ........................................... 378/16; 378/4
(58) Field of Search ....................................... 378/4–20

(56) References Cited

U.S. PATENT DOCUMENTS

| | | | |
|---|---|---|---|
| 5,103,469 A | | 4/1992 | Tanaka |
| 5,379,333 A | * | 1/1995 | Toth ............................ 378/16 |
| 5,400,378 A | | 3/1995 | Toth |
| 5,485,494 A | * | 1/1996 | Williams et al. .............. 378/16 |
| 5,696,807 A | | 12/1997 | Hsieh |
| 6,067,341 A | | 5/2000 | Horiuchi |
| 6,141,398 A | | 10/2000 | He et al. |
| 6,141,402 A | | 10/2000 | Toth |
| 6,404,844 B1 | | 6/2002 | Horiuchi et al. |
| 6,490,337 B1 | * | 12/2002 | Nagaoka et al. .............. 378/16 |

OTHER PUBLICATIONS

"Introduction To X–Ray Spectrometric Analysis" Eugene Bertin, Plenum Press, 1978, p 59.*

* cited by examiner

Primary Examiner—Craig E. Church
(74) Attorney, Agent, or Firm—Carl B. Horton, Esq.; Armstrong Teasdale LLP (57) ABSTRACT

For the purpose of reducing exposure of a subject to unnecessary radiation by controlling the tube current according to the X-ray emitting direction with respect to a region to be examined in the subject, a transmission area S is calculated from a cross-sectional plane (S801) and an ellipticity R is calculated for the cross-sectional plane (S802, S803). An image SD of a region having the transmission area S is then calculated (S804), and a SD ratio of a region having the ellipticity R is calculated (S805). An image SD of a region having the transmission area S and ellipticity R is then calculated using the image SD and the SD ratio (S806). Next, a target SD is specified (S807), and the tube current that controls X-rays emitted in the major-axis direction in the cross-sectional plane of the subject is calculated using the image SD obtained at S806 and the target SD (S808), and the tube current that controls X-rays emitted in the minor-axis direction in the cross-sectional plane of the subject is calculated using the obtained tube current and R (S809).

20 Claims, 8 Drawing Sheets

FIG. 1

| Target SD#1 | | Adult/Infant | | | | | 120kV/140kV | | | | | |
|---|---|---|---|---|---|---|---|---|---|---|---|---|
| | | | | | | Thickness | | | | | | |
| Anatomy | Mode | 10mm | 7mm | 6mm | 5mm | 4mm | 3mm | 2mm | 1mm | 0.5mm |
| 1 Head | IQ | 2.0 | 2.2 | 2.4 | 2.5 | 2.7 | 3.0 | 3.5 | 4.7 | 6.3 |
| | Normal | 2.2 | 2.4 | 2.6 | 2.8 | 3.0 | 3.3 | 3.8 | 5.2 | 7.0 |
| | Low Dose | 2.4 | 2.6 | 2.9 | 3.0 | 3.3 | 3.6 | 4.2 | 5.7 | 7.6 |
| 2 Orbit | IQ | 2.0 | 2.2 | 2.4 | 2.5 | 2.7 | 3.0 | 3.5 | 4.7 | 6.3 |
| | Normal | 2.2 | 2.4 | 2.6 | 2.8 | 3.0 | 3.3 | 3.8 | 5.2 | 7.0 |
| | Low Dose | 2.4 | 2.6 | 2.9 | 3.0 | 3.3 | 3.6 | 4.2 | 5.7 | 7.6 |
| 3 Neck | IQ | 3.6 | 4.0 | 4.3 | 4.6 | 4.9 | 5.3 | 6.3 | 8.5 | 11.4 |
| | Normal | 4.0 | 4.4 | 4.8 | 5.1 | 5.4 | 5.9 | 7.0 | 9.4 | 12.6 |
| | Low Dose | 4.4 | 4.9 | 5.2 | 5.6 | 6.0 | 6.5 | 7.7 | 10.4 | 13.9 |
| 4 Upper Extrem. | IQ | 5.4 | 6.0 | 6.4 | 6.8 | 7.3 | 8.0 | 9.4 | 12.7 | 17.1 |
| | Normal | 6.0 | 6.6 | 7.1 | 7.6 | 8.2 | 8.9 | 10.4 | 14.1 | 19.0 |
| | LowDose | 6.6 | 7.3 | 7.9 | 8.3 | 9.0 | 9.8 | 11.5 | 15.6 | 20.9 |
| 5 Chest | IQ | 5.4 | 6.0 | 6.4 | 6.8 | 7.3 | 8.0 | 9.4 | 12.7 | 17.1 |
| | Normal | 6.0 | 6.6 | 7.1 | 7.6 | 8.2 | 8.9 | 10.4 | 14.1 | 19.0 |
| | Low Dose | 6.6 | 7.3 | 7.9 | 8.3 | 9.0 | 9.8 | 11.5 | 15.6 | 20.9 |
| 6 Abdomen | IQ | 5.4 | 6.0 | 6.4 | 6.8 | 7.3 | 8.0 | 9.4 | 12.7 | 17.1 |
| | Normal | 6.0 | 6.6 | 7.1 | 7.6 | 8.2 | 8.9 | 10.4 | 14.1 | 19.0 |
| | LowDose | 6.6 | 7.3 | 7.9 | 8.3 | 9.0 | 9.8 | 11.5 | 15.6 | 20.9 |
| 7 Spine | IQ | 5.4 | 6.0 | 6.4 | 6.8 | 7.3 | 8.0 | 9.4 | 12.7 | 17.1 |
| | Normal | 6.0 | 6.6 | 7.1 | 7.6 | 8.2 | 8.9 | 10.4 | 14.1 | 19.0 |
| | Low Dose | 6.6 | 7.3 | 7.9 | 8.3 | 9.0 | 9.8 | 11.5 | 15.6 | 20.9 |
| 8 Pelvis | IQ | 5.4 | 6.0 | 6.4 | 6.8 | 7.3 | 8.0 | 9.4 | 12.7 | 17.1 |
| | Normal | 6.0 | 6.6 | 7.1 | 7.6 | 8.2 | 8.9 | 10.4 | 14.1 | 19.0 |
| | Low Dose | 6.6 | 7.3 | 7.9 | 8.3 | 9.0 | 9.8 | 11.5 | 15.6 | 20.9 |
| 9 Lower Extrem. | IQ | 5.4 | 6.0 | 6.4 | 6.8 | 7.3 | 8.0 | 9.4 | 12.7 | 17.1 |
| | Normal | 6.0 | 6.6 | 7.1 | 7.6 | 8.2 | 8.9 | 10.4 | 14.1 | 19.0 |
| | Low Dose | 6.6 | 7.3 | 7.9 | 8.3 | 9.0 | 9.8 | 11.5 | 15.6 | 20.9 |
| 10 misc | IQ | 5.4 | 6.0 | 6.4 | 6.8 | 7.3 | 8.0 | 9.4 | 12.7 | 17.1 |
| | Normal | 6.0 | 6.6 | 7.1 | 7.6 | 8.2 | 8.9 | 10.4 | 14.1 | 19.0 |
| | Low Dose | 6.6 | 7.3 | 7.9 | 8.3 | 9.0 | 9.8 | 11.5 | 15.6 | 20.9 |

X-RAY CT SYSTEM, GANTRY APPARATUS AND OPERATION CONSOLE

CROSS REFERENCE TO RELATED APPLICATIONS

This application claims the benefit of Japanese Application No. 2001-257757 filed Aug. 28, 2001.

BACKGROUND OF THE INVENTION

The present invention relates to an operation console for producing a tomographic image of a region to be examined based on projection data of the region to be examined, a gantry apparatus for emitting X-rays onto a region to be examined in a subject and generating projection data based on X-rays passing through the region to be examined, an X-ray CT system comprised of a gantry apparatus for emitting X-rays onto a region to be examined in a subject and generating projection data based on X-rays passing through the region to be examined and an operation console for producing a tomographic image of the region to be examined based on the projection data of the region to be examined obtained by the gantry apparatus, methods of controlling the operation console and the gantry apparatus, and a program code and a storage medium.

An X-ray CT system emits X-rays onto a subject (patient), detects the differences of X-ray absorption factors of human tissue in organs, blood, gray matters etc. by a detector, and provides an image (tomographic image) of a cross-sectional plane (a slice plane) of the region to be examined by computer-processing (reconstructing) the differences.

A physician diagnoses the condition etc. of the patient based on the tomographic image of the patient in a predefined region to be examined reconstructed by the X-ray CT system. To this end, the reconstructed tomographic image must have image quality that enables distinction of the differences of X-ray absorption factors of human tissue with good accuracy and that matches the purpose of the examination. To get such image quality, it is necessary to reduce image noise.

The image noise in the X-ray CT system is in general represented by the variance of CT values when a homogeneous material is imaged. (The variance will be referred to as an image SD hereinbelow.) A smaller image SD value corresponds to higher quality of a tomographic image, and a larger image SD value corresponds to lower quality of a tomographic image. To reduce the image noise and obtain a tomographic image with high quality (i.e., to reduce the image SD), the amount of transmitted X-rays that pass through the subject and are detected at the detector must be large; and hence, to obtain a sufficient amount of transmitted X-rays at the detector, the amount of X-rays emitted onto the subject must be large.

Paying attention only to improvement of the image quality and increasing the amount of the X-rays emitted onto the subject, however, undesirably leads to an increase of the exposure dose to the subject. Therefore, in practice, it is necessary to conduct control so that the amount of X-rays emitted from the X-ray tube is the minimum required to secure desired image quality.

The amount of X-rays emitted from the X-ray tube is controlled by the electric current passed to the X-ray tube (which will be referred to as the tube current or mA hereinbelow). Conventional X-ray CT systems are normally provided with functions for controlling the tube current to achieve such minimum X-ray emission, including an auto mA function (automatic tube current controlling function).

The auto mA function in the conventional X-ray CT systems involves: emitting beforehand a predetermined amount of X-rays in a predefined direction onto a predefined region for each subject (such a scan involving emitting beforehand X-rays for each subject to obtain desired data is sometimes referred to as a scout scan); calculating the image SD based on a measurement result with the amount of transmitted X-rays (baseline data) at that time; and establishing an image quality level required for a tomographic image for examination (such a target image quality level is sometimes referred to as a target SD); and calculating the tube current for examination based on the ratio of the image SD and target SD.

Figure 1:
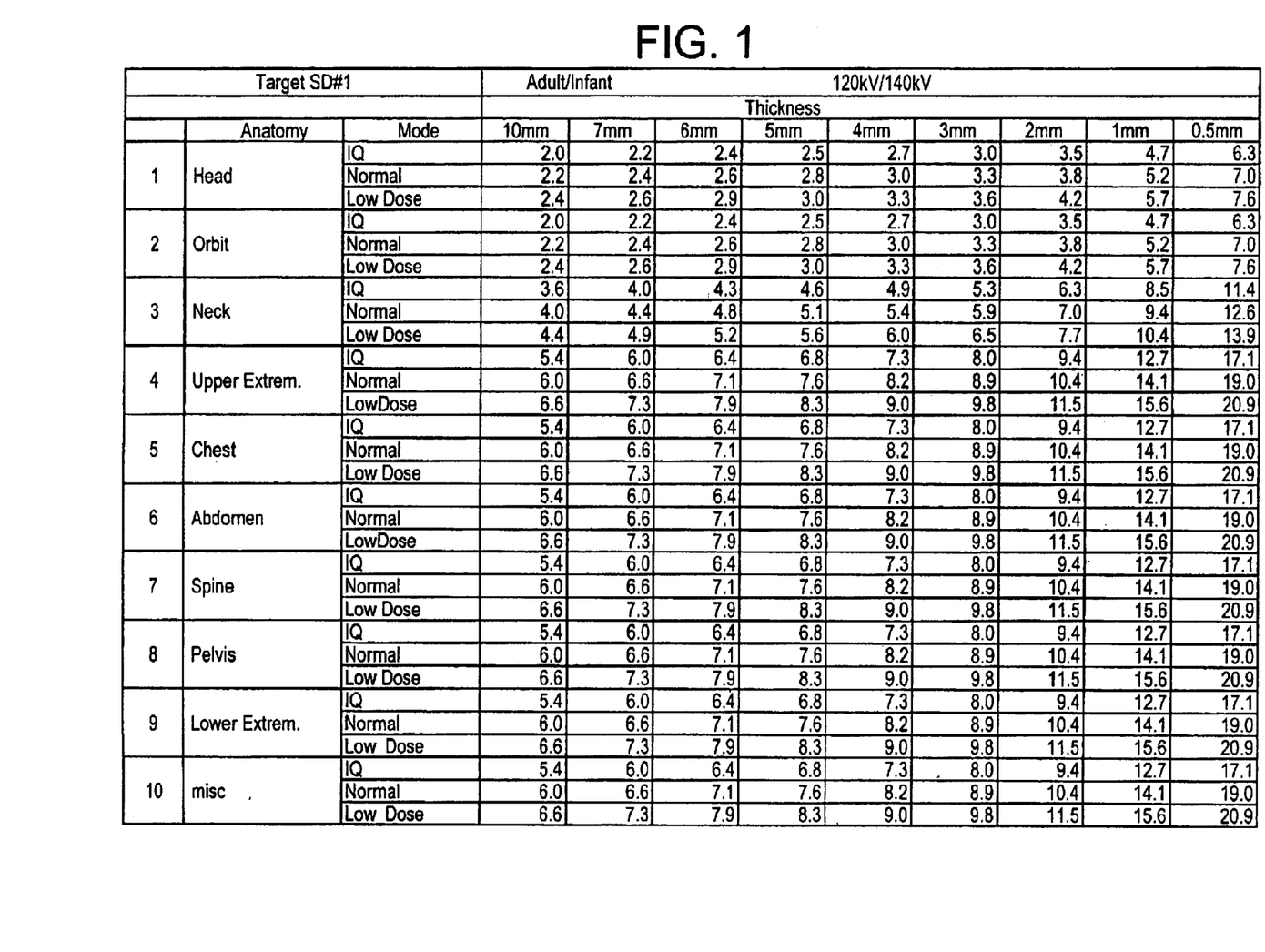
FIG. 1 shows an exemplary table for use in setting a target SD.

The target SD to be established is determined based on the slice thickness and the region to be examined for examination. Specifically, the target SD is determined with reference to a table as shown in FIG. 1. FIG. 1 shows an exemplary table for use in establishing the target SD.

For example, when the region to be examined is the chest and the slice thickness is 10 mm, the target SD value can be set to 5.4 referring to the table in FIG. 1 (in the mode IQ).

By employing the aforementioned tube current calculating method, the tube current matching the region to be examined can be calculated. By such a method, however, the region to be examined is exposed to X-rays corresponding to a constant tube current. Thus, excessive X-rays may be applied to the region to be examined depending upon the thickness thereof in some X-ray emitting directions. Consequently, the patient is exposed to unnecessary radiation.

SUMMARY OF THE INVENTION

Therefore, an object of the invention is to reduce the exposure of the subject to unnecessary radiation by controlling the tube current according to the X-ray emitting direction with respect to the region to be examined in the subject.

To attain the object of the present invention, an operation console of the present invention has, for example, a configuration as described below.

Specifically, there is provided an operation console for producing a tomographic image of a region to be examined based on projection data of said region to be examined, comprising: transmitting/receiving device for transmitting to an external apparatus instructions for collecting projection data, and receiving said projection data collected by said apparatus, wherein said external apparatus collects projection data at each scan position in a region to be examined in a subject by emitting X-rays in a predefined direction onto said region to be examined and carrying said subject; first calculating device for calculating a first control value for controlling the amount of X-rays emitted by said apparatus onto each scan position during a scan, based on the projection data at each scan position received by said transmitting/receiving device and the particulars of said instructions; and second calculating device for calculating a second control value for controlling the amount of X-rays according to the emitting angle of said X-rays emitted by said apparatus onto each scan position during a scan; wherein said transmitting/receiving device further transmits to said apparatus instructions for conducting a scan based on said first and second control values.

Said first calculating device calculates said first control value by correcting a control value for controlling the amount of X-rays in collecting projection data based on a target image quality level with respect to a tomographic image based on said projection data at each scan position.

When a tomographic image based on projection data at each scan position is approximated to an ellipse, said first control value controls the amount of X-rays emitted by said apparatus in the major-axis direction of said ellipse.

When a tomographic image based on projection data at each scan position is approximated to an ellipse, said second calculating device calculates said second control value by calculating the ratio of the major and minor axes of said ellipse and using said ratio and said first control value.

When a tomographic image based on projection data at each scan position is approximated to an ellipse, said second control value controls the amount of X-rays emitted in the minor-axis direction of said ellipse.

The particulars of said instructions are the region to be examined, slice thickness, and control value for controlling the amount of X-rays.

Said transmitting/receiving device transmits to said apparatus instructions for conducting a scan that periodically uses said first control value and said second control value.

Said first control value and said second control value represent the tube current passed to a controller for controlling the amount of X-rays when said apparatus emits said X-rays.

To attain the object of the present invention, a gantry apparatus of the present invention has, for example, a configuration as described below.

Specifically, there is provided a gantry apparatus for emitting X-rays onto a region to be examined in a subject, and generating scan data based on X-rays passing through said region to be-examined, comprising: transmitting/receiving device for receiving from an external apparatus instructions for collecting projection data at each scan position in a region to be examined in a subject by emitting X-rays in a predefined direction onto said region to be examined and carrying said subject, transmitting the collected projection data to said apparatus, and receiving from said apparatus scan instructions for controlling the amount of X-rays according to the emitting angle of said X-rays onto each scan position; and control device for conducting control over the amount of X-rays according to the emitting angle of said X-rays emitted onto said region to be examined based on said scan instructions received by said transmitting/receiving device.

Therefore, the present invention can control the tube current according to the X-ray emitting direction with respect to a region to be examined in a subject, and can reduce exposure of the subject to unnecessary radiation.

Further objects and advantages of the present invention will be apparent from the following description of the preferred embodiments of the invention as illustrated in the accompanying drawings.

DETAILED DESCRIPTION OF THE INVENTION

The present invention will now be described in detail according to preferred embodiments with reference to the accompanying drawings.

First Embodiment

Figure 2:
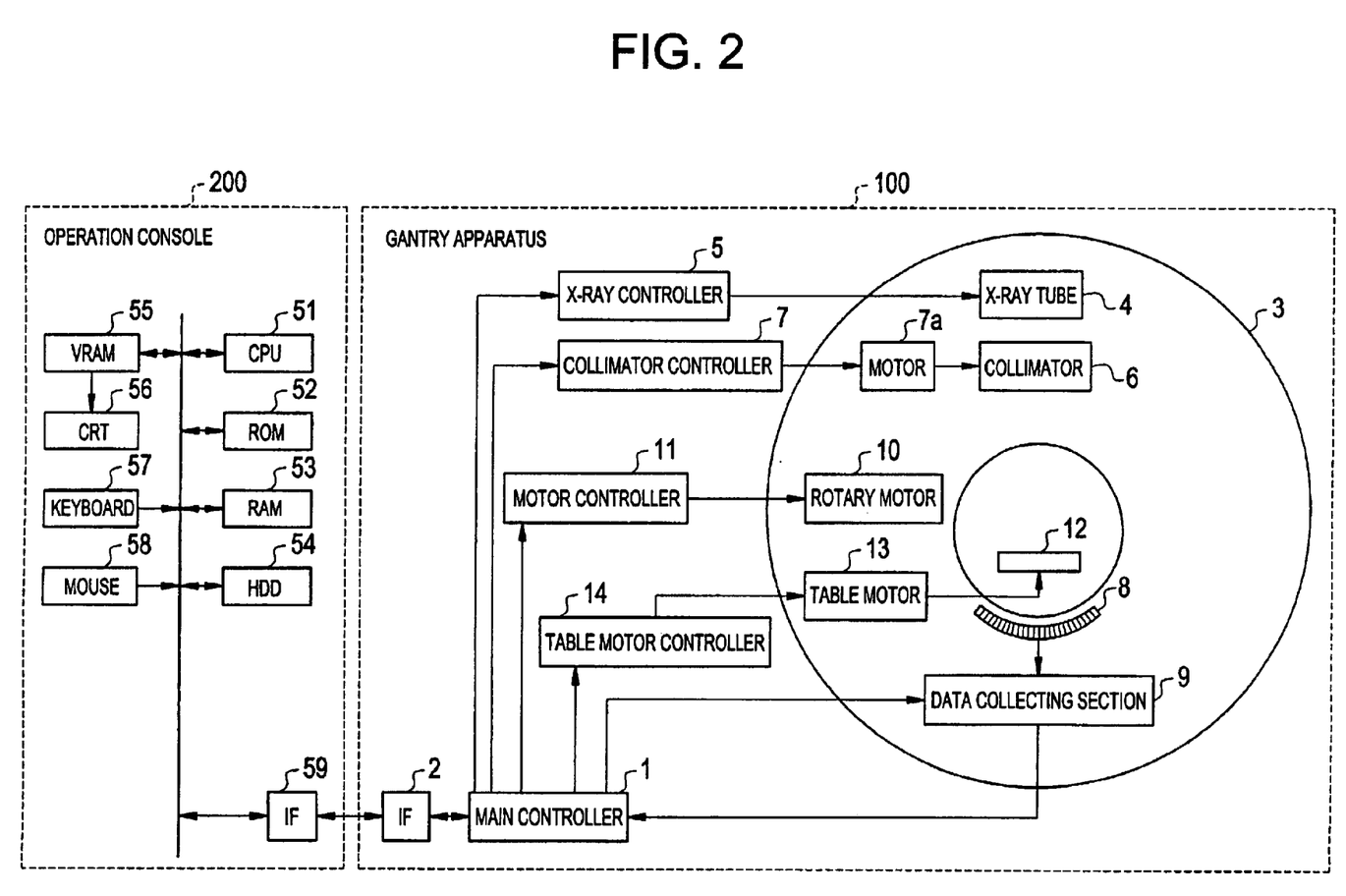
FIG. 2 is a block configuration diagram of an X-ray CT system in accordance with a first embodiment of the present invention.

FIG. 2 is a block configuration diagram of an X-ray CT system of a first embodiment. As shown, the system is comprised of a gantry apparatus 100 that is integrally attached with an X-ray detecting mechanism for emitting X-rays onto a subject and detecting X-rays passing through the subject, and an operating console 200 for performing several kinds of operating settings for the gantry apparatus 100 and reconstructing an X-ray tomographic image based on data output from the gantry apparatus 100 for display.

The gantry apparatus 100 comprises a main controller 1 for controlling the entire apparatus 100, and the components discussed in the following.

Reference numeral 2 designates an interface for communicating with the operating console 200, and 3 designates a gantry having a cavity portion for carrying a subject (patient) laid on a table 12 (in a direction perpendicular to the drawing plane, which direction will be sometimes referred to as a z-axis hereinbelow), and comprising therein an X-ray tube 4 which is an X-ray source (driven and controlled by an X-ray tube controller 5), a collimator 6 having a slit for defining the X-ray emission range, and a motor 7a for adjusting the width of the slit in the collimator 6 for defining the X-ray emission range. The drive for the motor 7a is controlled by a collimator controller 7.

The gantry 3 also comprises an X-ray detecting section 8 for detecting X-rays passing through the subject, and a data collecting section 9 for collecting projection data obtained by the transmitted X-rays captured by the X-ray detecting section 8. The X-ray tube 4 and collimator 6, and the X-ray detecting section 8 are disposed across the cavity portion, i.e., disposed at opposed positions across the subject, and they rotate around the gantry 3 with their relationship maintained. The rotation is conducted by a rotary motor 10 driven by driving signals from a motor controller 11. The table 12 for resting the subject is carried in the z-axis direction, and the drive of this carrying is conducted by a table motor 13. The drive of the table motor 13 is controlled by a table motor controller 14.

The main controller 1 analyzes several kinds of commands received via the interface 2, and based upon the analysis, it outputs several kinds of control signals to the X-ray tube controller 5, collimator controller 7, motor controller 11, table motor controller 14 and data collecting section 9. The main controller 1 also conducts processing of sending the projection data collected at the data collecting section 9 to the operation console 200 via the interface 2.

The operating console 200 is what is commonly referred to as a workstation, comprising a CPU 51 for controlling the entire apparatus, a ROM 52 storing a boot program etc., a RAM 53 that serves as a main storage device, as shown, and the components discussed in the following.

An HDD 54 is a hard disk device, which stores an OS, a scan control program which will be described later, and a diagnosis program for supplying several kinds of instructions to the gantry apparatus 100 and reconstructing an X-ray tomographic image based on data received from the gantry apparatus 100. A VRAM 55 is a memory for developing image data to be displayed, and the image data can be displayed on a CRT 56 by developing the image data and the like there. Reference numerals 57 and 58 designate a keyboard and a mouse for performing several kinds of settings. Reference numeral 59 designates an interface for communicating with the gantry apparatus 100.

The auto mA executed by the X-ray CT system according to the present embodiment having the aforementioned configuration will now be described.

First, a scout scan is performed on a region to be examined in the subject rested on the table 12. A method of calculating the tube current for use in a scan (which is performed after the scout scan) at a scout scan position of interest among a plurality of scout scan positions that have been subjected to the scout scan, will be described below.

Figure 3:
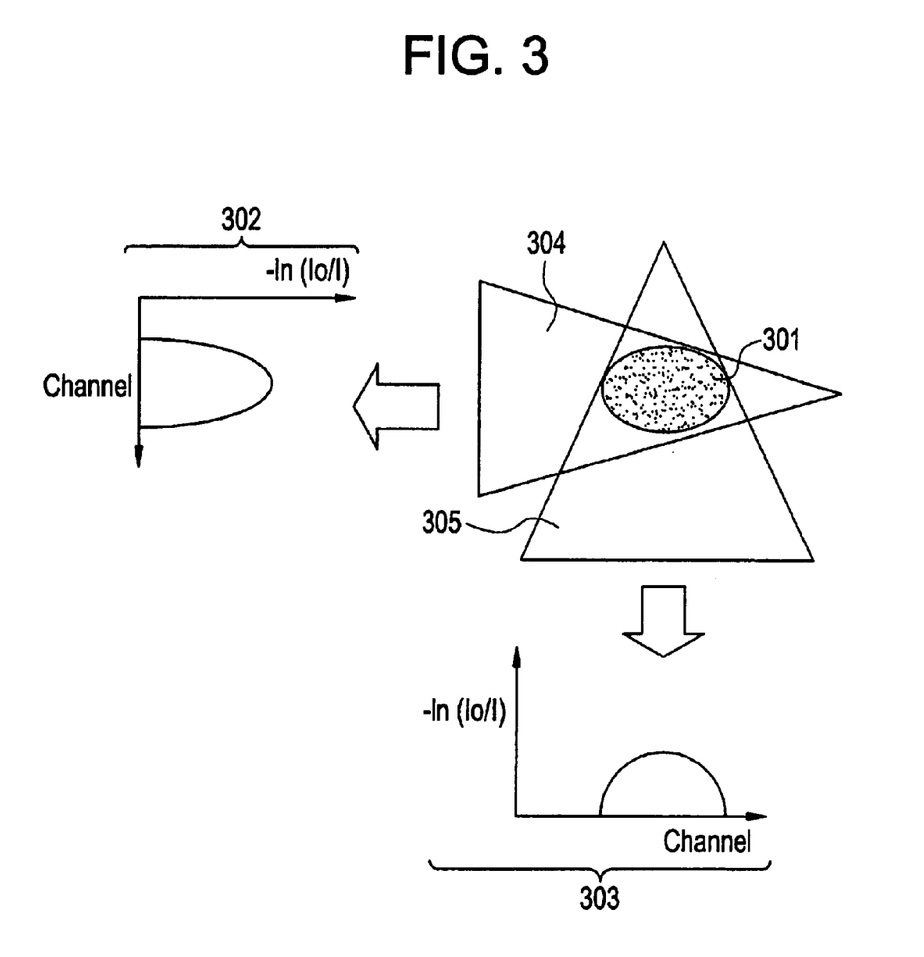
FIG. 3 shows graphs obtained in performing a scout scan.

FIG. 3 shows graphs obtained in performing the scout scan. In FIG. 3, reference numeral 301 designates a cross-sectional plane of a region to be examined at a scout scan position of interest (which will be referred to simply as a cross-sectional plane), and the cross-sectional plane is approximated to an ellipse. Reference numeral 302 designates a graph obtained in performing the scout scan by X-rays 304 on the region to be examined at the scout scan position of interest along a major-axis direction of the cross-sectional plane 301. Reference numeral 303 designates a graph obtained in performing the scout scan by X-rays 305 on the region to be examined at the scout scan position of interest along a minor-axis direction of the cross-sectional plane 301. That is, the graphs 302 and 303 are those obtained in performing the scout scan on the region to be examined at the scout scan position of interest with gantry 3 rotation angles shifted by 90°. The vertical axes in these graphs represent the ratio in a logarithmic form of the amount of X-rays (Io) emitted onto the region to be examined at the scout scan position of interest and the amount of X-rays (I) having passed through the region to be examined at the scout scan position of interest, and the horizontal axes represent the channel of the X-ray detecting section 8.

Figure 4A:
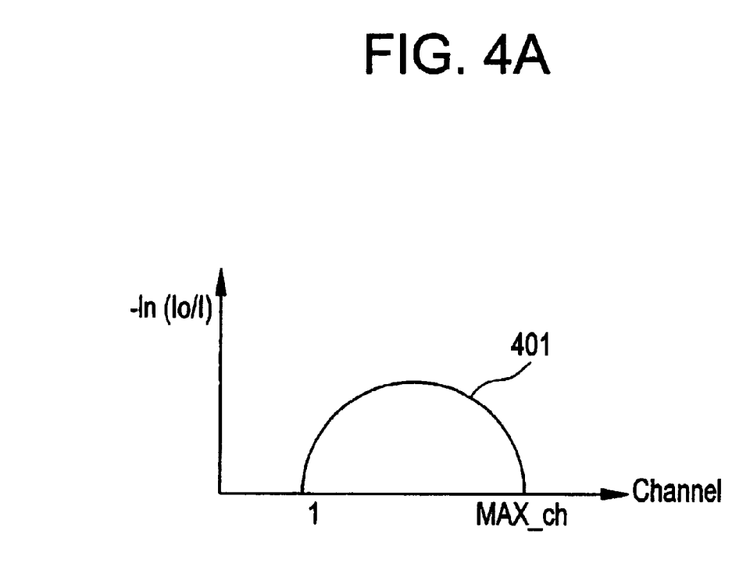
FIG. 4 shows the graphs 302 and 303 in detail.
Figure 4B:
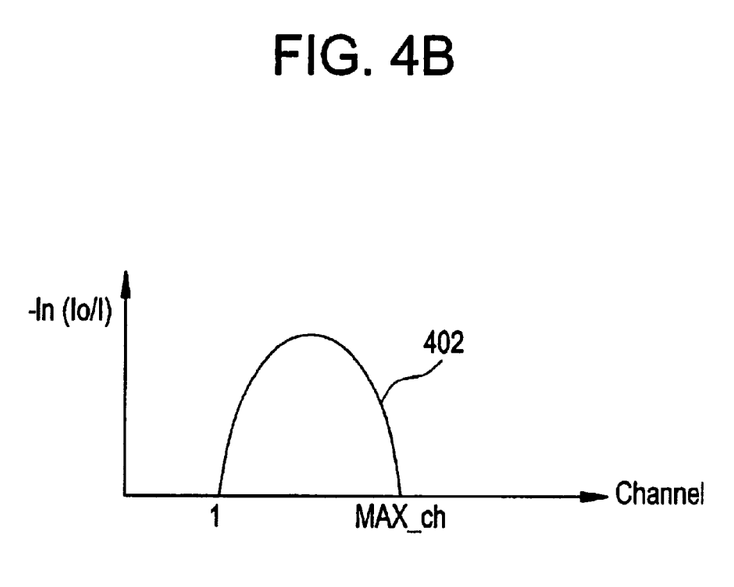

Details of the graphs 302 and 303 are shown in FIGS. 4(*a*) and (*b*), respectively. In these figures, the channel is designated by numbers 1 through MAX_ch, and sets (regions) of −ln(Io/I) for the channels are designated by reference numerals 401 and 402. The area S (which will be referred to as transmission area hereinbelow) of the region 401 or 402 is given by the following equation:

$$S = pr(1) + pr(2) + \ldots + pr(MAX\_ch),$$

where pr(i) (1≤i≤MAX_ch) represents the value of −ln (Io/I) for a channel i. The transmission area of the region 401 will be represented as S1, and that of the region 402 as S2 hereinbelow.

Figure 5A:
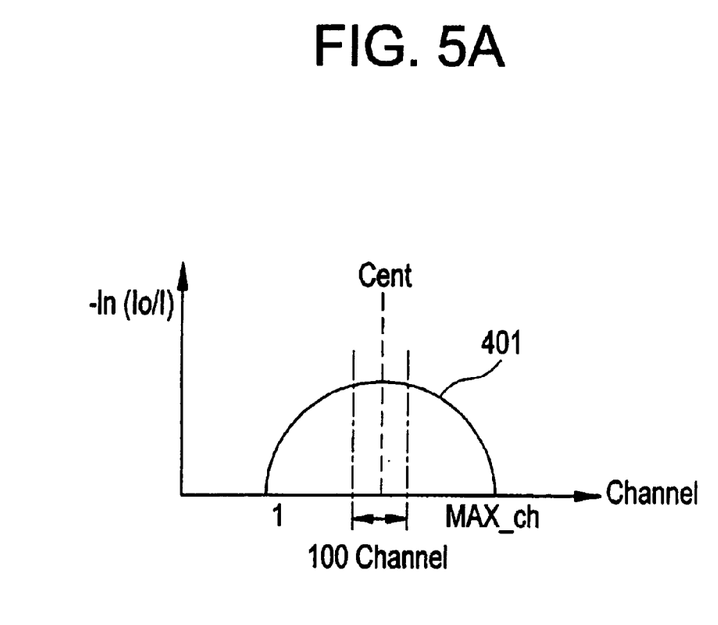
FIG. 5 is a diagram for explaining a method of calculating the minor and major axes of the cross-sectional plane 301.
Figure 5B:
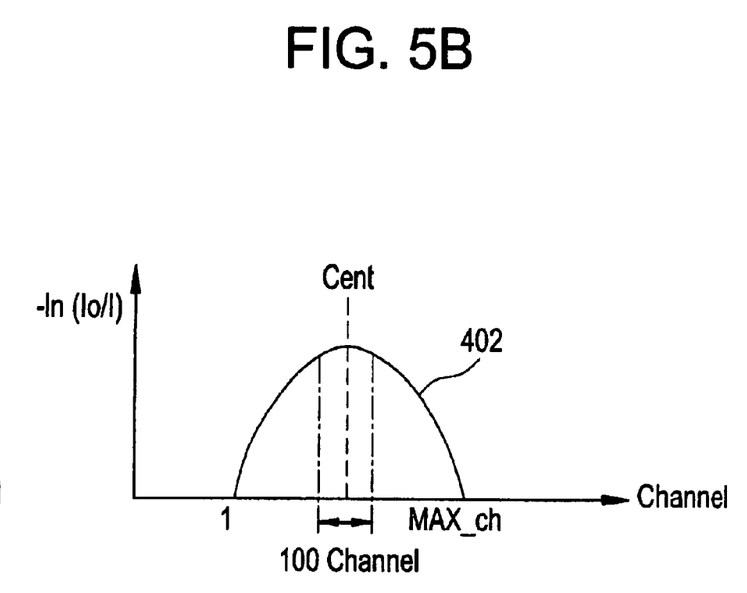

Next, the ratio of the minor axis and major axis (i.e., the ellipticity) of the cross-sectional plane 301 is calculated. This calculation is equivalent to calculating the ratio of −ln(Io/I) values corresponding to detectors (channels) that detect X-rays passing through and near the major and minor axes of the cross-sectional plane 301 in the graphs 302 and 303. A method of calculating the major and minor axes of the cross-sectional plane 301 will now be described with reference to FIG. 5. FIG. 5 is a diagram for explaining the method of calculating the major and minor axes of the cross-sectional plane 30.

First, −ln(Io/I) for 50 front channels and 50 rear channels with respect to a central channel (Cent) among all the channels are summed up. This calculation can be achieved as follows:

$$r = pr(Cent - 49) + pr(Cent - 48) + \ldots + pr(Cent + 49) + pr(Cent + 50)$$

The r's in the region 401 and 402 are calculated, and the results of the calculation are represented as r1 and r2, respectively. As a result, since r1 and r2 are the respective sums of −ln(Io/I) at and near the minor and major axes of the cross-sectional plane 301, the aforementioned ellipticity R can be obtained from the ratio (r1/r2):

$$R = r1/r2.$$

A method of calculating the tube current using S1 (or S2) and R thus obtained will now be described. As stated above, the tube current can be calculated by obtaining the image SD and the target SD, and calculating their ratio. Accordingly, a method of calculating the image SD will first be described.

The image SD varies with the transmission area and the ellipticity. Therefore, the image SD can be calculated from the transmission area and the ellipticity obtained as above. The image SD $\rho_{px}$ of a region having the transmission area S can be calculated according to the following equation:

$$\rho_{px} = \alpha + \beta \times S + \gamma \times S^2,$$

where $\alpha$, $\beta$ and $\gamma$ are predetermined constants. Moreover, the SD ratio k of a region having the ellipticity R can be obtained by following equation:

$$k = A + B \times R^2,$$

where A and B are predetermined constants. Using $\rho_{px}$ and k obtained as above, the image SD ($\rho'_{px}$) of a region having the transmission area S and the ellipticity R is calculated as below:

$$\rho'_{px} = \rho_{px} \times k.$$

On the other hand, the target SD can be uniquely determined from the table shown in FIG. 1 by selecting the region to be examined, slice thickness and mode (from among three modes of IQ, Normal and LowDose in the example of FIG. 1), as described earlier. In this example, the region to be examined on which the scout scan has been performed, and the slice thickness and mode specified in performing the scout scan are employed. Representing the determined target SD as $\rho_{target}$, the tube current value to be ultimately obtained can be calculated based on the following equation:

$$mA = (mA_{reference} \times tf)/(\rho'_{px}/\rho_{target})^2,$$

where $mA_{reference}$ is the tube current that was passed to the X-ray tube 4 when the scout scan was performed, and tf is a calculated value of 10/(slice thickness).

However, since the tube current thus obtained does not take the aforementioned thickness of the region to be examined in the X-ray emitting direction into account, the tube current may be more than required for some thicknesses of the region to be examined. For example, when the cross-sectional plane of a region to be examined is approximated to an ellipse and the region to be examined is exposed to X-rays corresponding to the same tube current, the amount of the X-rays may be excessive in the minor-axis direction of the cross-sectional plane even though it is appropriate in the major-axis direction.

Accordingly, the tube current obtained as above is called a first control value, which is used as the tube current in emitting X-rays in the major-axis direction (represented as $mA_t$ hereinbelow) in this embodiment. On the other hand, the tube current in emitting X-rays in the minor-axis direction (represented as $mA_b$ hereinbelow) is calculated based on the following equation:

$$mA_b = mA_t \times R.$$

This tube current is called a second control value. Thus, the tube current can be controlled in emitting X-rays in the major-axis and minor-axis directions, and as a result, X-rays corresponding to the controlled tube current can be emitted.

Moreover, the tube current varies each time X-rays are emitted in the major-axis and minor-axis directions of the cross-sectional plane as described above. In other words, the first and second control values (tube current values $mA_t$ and $mA_b$) are changed each time the rotation angle of the gantry 3 varies by 90°. Therefore, when the rotation angle of the gantry 3 is represented as $\theta$, and a function for determining the tube current value as $f(\theta)$, the function f can be expressed as follows:

$$f(\theta) = mA_t(1-R)\sin(\theta) + mA_t R$$

Figure 6:
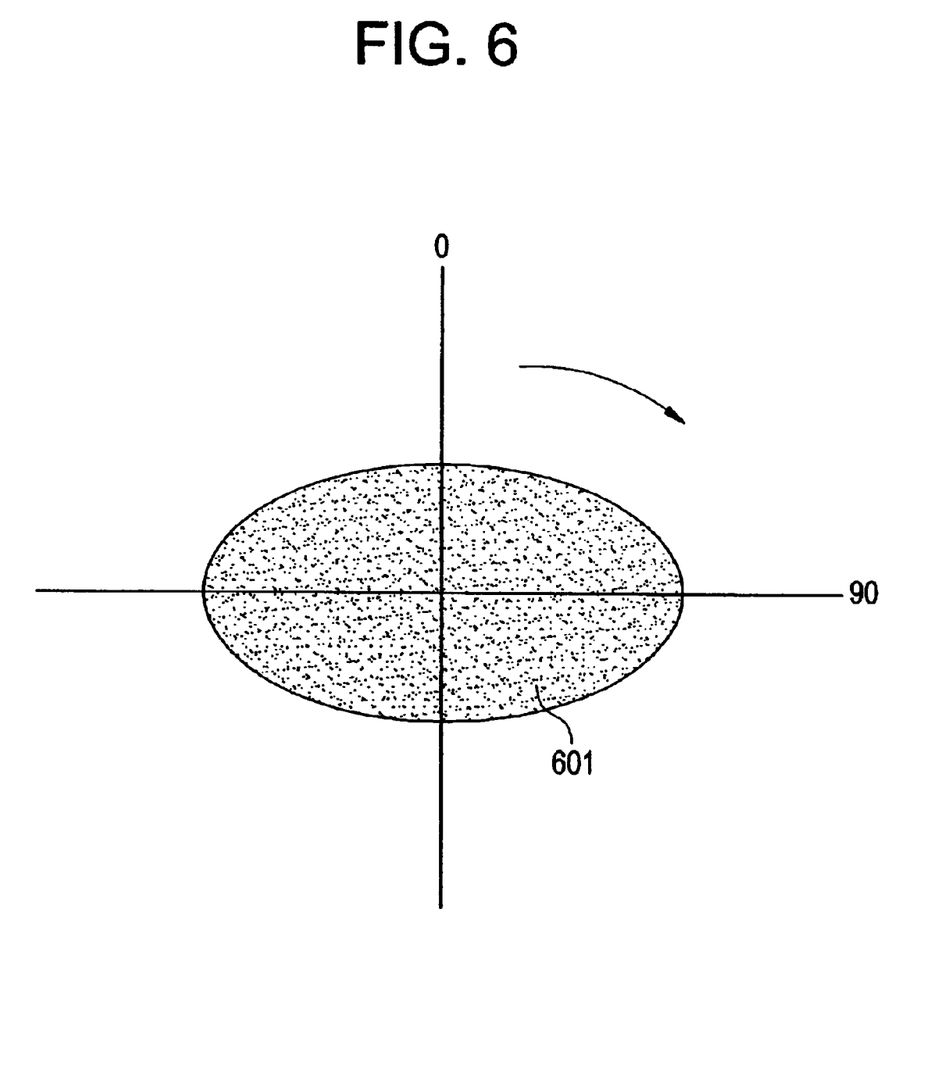
FIG. 6 is a diagram for explaining $\theta$.

$\theta$ is defined as 0° in the minor-axis direction of the cross-sectional plane 601 of the region to be examined, and as 90° in the major-axis direction, as shown in FIG. 6. However, the function for determining the tube current value is not limited to the sine function, but may be any appropriate periodic function having a phase of 90°, including a cosine function and triangular wave.

By the aforementioned processing, the function, for determining the tube current value for use in performing a scan at a scout scan position of interest (or a scan position) in a region to be examined can be calculated. Moreover, by performing the aforementioned processing on every scout scan position in the region to be examined, the function for determining the tube current value suitable for each scout scan position can be calculated; and by performing a scan at each scout scan position using the calculated function, exposure of the region to be examined to unnecessary radiation can be reduced.

Figure 7:
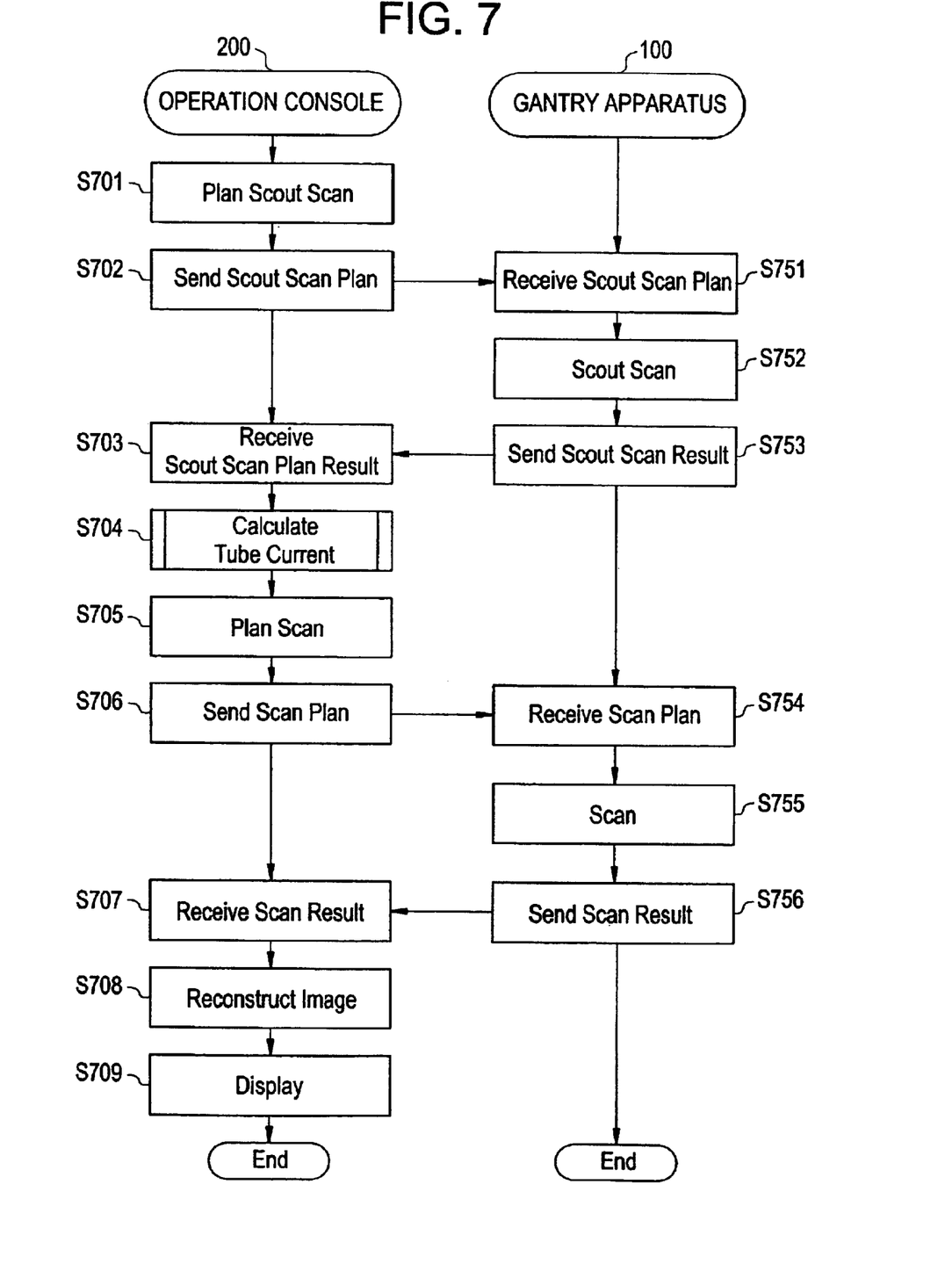
FIG. 7 is a flow chart of processing for calculating a function for determining the tube current value, and obtaining an X-ray tomographic image based on the calculated tube current.
Figure 8:
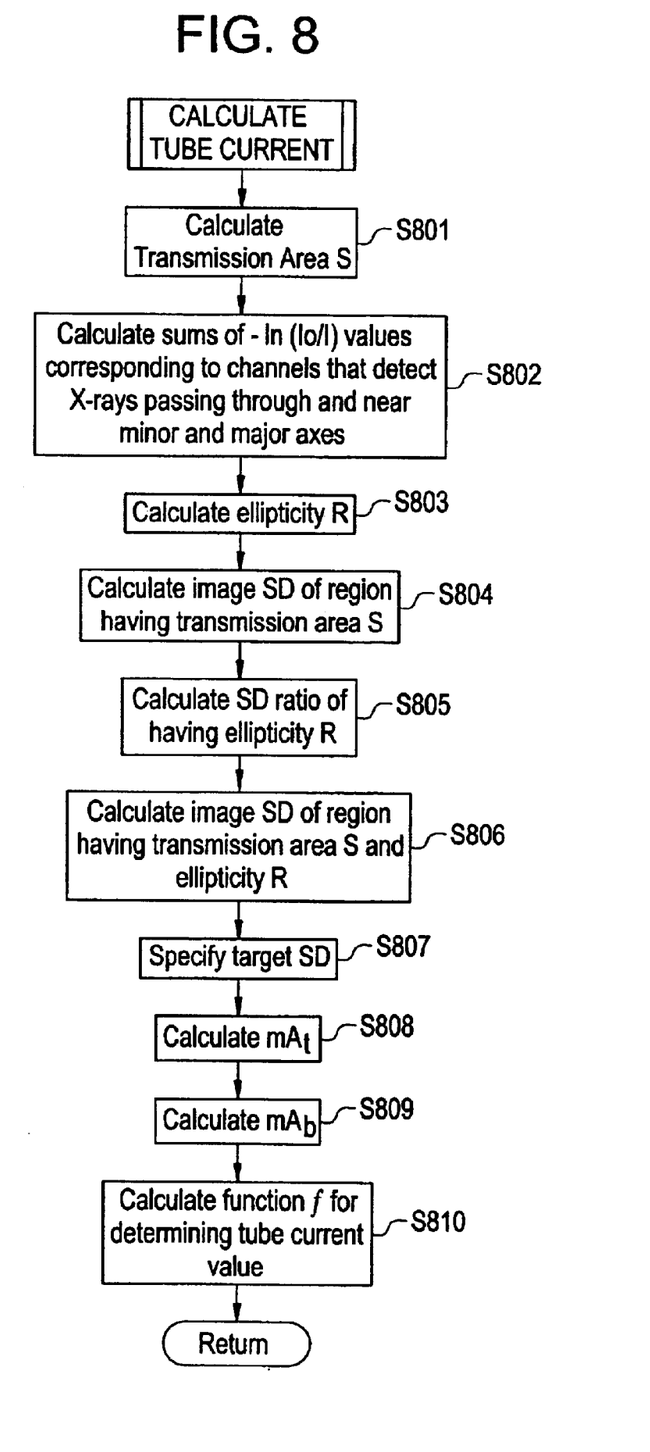
FIG. 8 is a flow chart showing processing at Step 704 in detail.

FIGS. 7 and 8 show flow charts of the processing described above for calculating the function for determining the tube current value and obtaining an X-ray tomographic image based on the calculated tube current.

In FIG. 7, a scout scan plan is first input using the keyboard 57 and mouse 58 from the operation console 200 (Step S701). The scout scan plan includes the region to be examined in the subject of the scout scan, the tube current, the slice thickness and the like. The input scout scan plan is next sent to the gantry apparatus 100 (Step S702). The gantry apparatus 100 receives the scout scan plan sent by the operation console 200 (Step S751), and performs a scout scan based on the received scout scan plan (Step S752). The gantry apparatus 100 then sends the result of the scout scan (projection data) to the operation console 200 (Step S753). The operation console 200 receives the result of the scout scan sent by the gantry apparatus 100 (Step S703), and calculates a function for determining the tube current value for each scout scan position by executing the aforementioned processing based on the result (Step S704). Although not shown, an X-ray tomographic image is produced from the projection data contained in the received scout scan result at Step S703.

The processing at Step S704 is shown in FIG. 8 in detail and will be described below.

First, a transmission area S (either S1 or S2 in the example shown in FIG. 3) is calculated from the cross-sectional plane (Step S801). Next, the sums r1 and r2 of −ln(Io/I) are calculated corresponding to channels that detect X-rays passing through and near the minor and major axes of the cross-sectional plane (Step S802). The ellipticity R of the cross-sectional plane is then calculated using the calculated r1 and r2 (Step S803). Then, an image SD ($\sigma_{px}$) of a region having the transmission area S is calculated using the transmission area S obtained at Step S801 (Step S804), and a SD ratio (k) of a region having the ellipticity R is calculated using the ellipticity R obtained at Step S803 (Step S805).

Then, an image SD ($\sigma'_{px}$) of a region having the transmission area S and the ellipticity R is calculated using the image SD ($\sigma_{px}$) obtained at Step S804 and the SD ratio (k) obtained at Step S805 (Step S806). A target SD is next specified from the table shown in FIG. 2 by using the keyboard 57 and the mouse 58 to input the region to be examined, slice thickness and mode (Step S807). The processing at Step S807 may be executed when the scout scan plan is input at Step S701.

Next, $mA_t$ is calculated using the image SD ($\sigma'_{px}$) obtained at Step S806 and the target SD ($\sigma_{target}$) specified at Step S807 (Step S808), and $mA_b$ is calculated using the calculated $mA_t$ and the ellipticity R (Step S809). A function for determining the tube current value is then calculated using the obtained $mA_t$ and $mA_b$ (Step S810). Although not shown, the processing of calculating the function f at the scout scan position of interest shown in FIG. 8 is executed for all the scout scan positions in the region to be examined, and after the functions f are obtained for all the scout scan positions in the region to be examined, the processing proceeds to Step S705.

Returning to FIG. 7, a scan plan is input using the keyboard 57 and the mouse 58 (Step S705), and the scan plan including the functions f calculated at Step S704 is sent to the gantry apparatus 100 (Step S706). The gantry apparatus 100 receives the scan plan sent by the operation console 200 (Step S754), and performs a scan based on the received scan plan (Step S755). At the same time, the gantry apparatus 100 sends the functions f included in the received scan plan to the X-ray controller 5, and performs control over the tube current based on the functions f. Consequently, the X-ray tube 4 emits X-rays based on the controlled tube current.

Then, the result of the scan (scan data) is sent to the operation console 200 (Step S756), and the operation console 200 receives the result of the scan sent by the gantry apparatus 100 (Step S707). The operation console 200 then produces an X-ray tomographic image from the received scan data by image reconstruction (Step S708), and displays the X-ray tomographic image on the CRT 56 (Step S709).

In the processing described above, the first and second control values are calculated by the CPU 51, which serves as first calculating device for calculating the first control value and second calculating device for calculating the second control value, in the operation console 200.

Other Embodiments

The object of the present invention can also be achieved by providing a system or apparatus with a storage medium (or record medium) that is recorded with a software program code for implementing the function of the aforementioned embodiment, and reading out and executing the program code stored in the storage medium by a computer (or CPU or MPU) in the system or apparatus. In this case, the program code per se read out from the storage medium implements the function of the aforementioned embodiment, and therefore, the storage medium storing the program code constitutes the present invention. Moreover, not only that the function of the aforementioned embodiment is implemented by executing the read-out program code by the computer (operation console), but the case in which an operating system (OS), for example, running on the computer performs part or all of the actual processing based on instructions by the program code, and the processing implements the function of the aforementioned embodiment, is also included.

When the present invention is applied to such a storage medium, the storage medium is configured to store a program code corresponding to part or all of the aforementioned flow charts (shown in FIG. 7 and/or FIG. 8).

Storage media usable for storing such a program code include, for example, a floppy disk, hard disk, optical disk, magneto-optical disk, CD-ROM, magnetic tape, non-volatile memory card and ROM. Furthermore, such a program code may be downloaded via a medium such as a network (e.g., the Internet).

Many widely different embodiments of the invention may be configured without departing from the spirit and the scope of the present invention. It should be understood that the present invention is not limited to the specific embodiments described in the specification, except as defined in the appended claims.

What is claimed is:

1. An operation console for producing a tomographic image of a region to be examined based on projection data of said region to be examined, comprising:

a transmitting/receiving device for transmitting to an external apparatus instructions for collecting projection data, and receiving said projection data collected by said apparatus, wherein said external apparatus collects projection data at each scan position in a region to be examined in a subject by emitting X-rays in a predefined direction onto said region to be examined and carrying said subject;

a first calculating device for calculating a first control value for controlling the amount of X-rays emitted by said apparatus on each scan position during a scan, based on the projection data at each scan position received by said transmitting/receiving device and the particulars of said instructions, wherein the first control value ($mA_t$) comprises a predetermined target image quality level ($\rho_{target}$);

a second calculating device for calculating a second control value for controlling the amount of X-rays according to the emitting angle of said X-rays emitted by said apparatus onto each scan position during a scan, wherein the second control value ($mA_b$) is defined in accordance with $$mA_b = mA_t \times R$$

where $mA_t$ is the first control value, and

R is a ellipticity of an object scanned; and wherein said transmitting/receiving device further transmits to said apparatus instructions for conducting a scan based on a ratio of said first and second control values.

2. The operation console of claim 1, wherein said first calculating device calculates said first control value by correcting a control value for controlling the amount of X-rays in collecting projection data based on a target image quality level with respect to a tomographic image based on said projection data at each scan position.

3. The operation console of claim 2, wherein, when a tomographic image based on projection data at each scan position is approximated to an ellipse, said first control value controls the amount of X-rays emitted by said apparatus in the major-axis direction of said ellipse.

4. The operation console of claim 1, wherein, when a tomographic image based on projection data at each scan position is approximated to an ellipse, said second calculating device calculates said second control value by calculating the ratio of the major and minor axes of said ellipse and using said ratio and said first control value.

5. The operation console of claim 4, wherein, when a tomographic image based on projection data at each scan position is approximated to an ellipse, said second control value controls the amount of X-rays emitted in the minor-axis direction of said ellipse.

6. The operation console of claim 1, wherein the particulars of said instructions are the region to be examined, slice thickness, and control value for controlling the amount of X-rays.

7. The operation console of claim 1, wherein said transmitting/receiving device transmits to said apparatus instructions for conducting a scan that periodically uses said first control value and said second control value.

8. The operation console of claim 1, wherein said first control value and said second control value represent the tube current passed to a controller for controlling the amount of X-rays when said apparatus emits said X-rays.

9. A gantry apparatus for emitting X-rays onto a region to be examined in a subject, and generating scan data based on X-rays passing through said region to be examined, comprising:

a transmitting/receiving device for receiving from an external apparatus instructions for collecting projection data at each scan position in a region to be examined in a subject by emitting X-rays in a predefined direction onto said region to be examined and carrying said subject, transmitting the collected projection data to said apparatus, and receiving from said apparatus scan instructions for controlling the amount of X-rays according to the emitting angle of said X-rays onto each scan position;

a control device for conducting control over the amount of X-rays according to the emitting angle of said X-rays emitted onto said region to be examined based on said scan instructions received by said transmitting/receiving device;

a first calculating device for calculating a first control value wherein the first control value ($mA_t$) comprises a predetermined target image quality level ($\rho_{target}$);

a second calculating device for calculating a second control value for controlling the amount of X-rays according to the emitting angle of said X-rays emitted by said apparatus onto each scan position during a scan, wherein the second control value ($mA_b$) is defined in accordance with $$mA_b = mA_t \times R$$

where $mA_t$ is the first control value, and

R is a ellipticity of an object scanned; and
wherein said transmitting/receiving device further transmits to said apparatus instructions for conducting a scan based on a ratio of said first and second control values.

10. An X-ray CT system comprised of a gantry apparatus for emitting X-rays onto a region to be examined in a subject, and generating scan data based on X-rays passing through said region to be examined, and an operation console for producing a tomographic image of said region to be examined based on the scan data of said region to be examined obtained by said gantry apparatus, wherein
said operation console comprises:
a first transmitting/receiving device for transmitting to said gantry apparatus instructions for collecting projection data, and receiving said projection data collected by said gantry apparatus, wherein said gantry apparatus collects projection data at each scan position in a region to be examined in a subject by emitting X-rays in a predefined direction onto said region to be examined and carrying said subject;
a first calculating device for calculating a first control value for controlling the amount of X-rays emitted by said gantry apparatus onto each scan position during a scan, based on the projection data at each scan position received by said first transmitting/receiving device and the particulars of said instructions, wherein the first control value ($mA_t$) is defined in accordance with:

$$mA_t = (mA_{reference} \times tf)/(\rho'_{px}/\rho_{target})^2$$

where
$mA_{reference}$ is a tube current used during a scout scan,
tf is a calculated value of 10/slice thickness,
$\rho'_{px}$ is a baseline image quality level, and
$\rho_{target}$ is a target image quality level; and
a second calculating device for calculating a second control value for controlling the amount of X-rays according to the emitting angle of said X-rays emitted by said gantry apparatus onto each scan position during a scan, wherein the second control value ($mA_b$) is defined in accordance with $$mA_b = mA_t \times R$$

where
$mA_t$ is the first control value, and
R is a ellipticity of an object scanned;
wherein said first transmitting/receiving device further transmits instructions for conducting a scan based on a ratio of said first and second control values to said gantry apparatus; and
said gantry apparatus comprises:
a second transmitting/receiving device for receiving from said operation console instructions for collecting projection data at each scan position in a region to be examined in a subject by emitting X-rays in a predefined direction onto said region to be examined and carrying said subject, transmitting the collected projection data to said operation console, and receiving from said operation console scan instructions for controlling the amount of X-rays according to the emitting angle of said X-rays onto each scan position; and
a control device for conducting control over the amount of X-rays according to the emitting angle of said X-rays emitted onto said region to be examined based on said scan instruction received by said second transmitting/receiving device.

11. A gantry apparatus in accordance with claim 9 further comprising a second calculating device that calculates a second control value for controlling an amount of said X-rays according to an emitting angle of said X-rays.

12. A gantry apparatus in accordance with claim 11 wherein the second control value is a function of the first control value and ellipticity of said region to be examined.

13. A gantry apparatus in accordance with claim 9 wherein the first control value is a function of a tube current passed to an X-ray tube of said gantry apparatus during a scout scan, an image variance of an image obtained using said gantry apparatus, and a target variance.

14. A gantry apparatus in accordance with claim 13 wherein the image variance is dependent upon ellipticity of said region to be examined and a transmission area of said gantry apparatus.

15. A gantry apparatus in accordance with claim 14 wherein the transmission area is a sum of logarithmic values.

16. A gantry apparatus in accordance with claim 15 wherein each of the logarithmic values is obtained by performing scout scans, and wherein each of the scout scans is performed at a gantry angle shift by at least one degree compared to a gantry angle of remaining scout scans.

17. A gantry apparatus in accordance with claim 13 wherein the target variance is determined from a table that lists a type of said region to be examined, slice thickness, and mode.

18. A gantry apparatus in accordance with claim 9 wherein, when an image based on projection data at each scan position is approximated to be an ellipse, the first control value controls the amount of X-rays emitted by said gantry apparatus in a major-axis direction of the ellipse.

19. A gantry apparatus in accordance with claim 9 wherein, when an image based on projection data at each scan position is approximated to be an ellipse, a second calculating device calculates a second control value by calculating a ratio of a major and minor axes of the ellipse and using the ratio and the first control value.

20. A gantry apparatus in accordance with claim 9 wherein, when an image based on projection data at each scan position is approximated to be an ellipse, a second control value controls the amount of X-rays emitted in a direction of a minor axis of the ellipse.

* * * * *